United States Patent
Mori

(10) Patent No.: US 9,149,212 B2
(45) Date of Patent: Oct. 6, 2015

(54) WALKING POSTURE DETERMINATION APPARATUS

(75) Inventor: Kentaro Mori, Nagaokakyo (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 951 days.

(21) Appl. No.: 13/338,821

(22) Filed: Dec. 28, 2011

(65) Prior Publication Data

US 2012/0101771 A1    Apr. 26, 2012

Related U.S. Application Data

(63) Continuation of application No. PCT/JP2010/067365, filed on Oct. 4, 2010.

(30) Foreign Application Priority Data

Oct. 6, 2009   (JP) ................................ 2009-232673

(51) Int. Cl.
| | |
|---|---|
| G06F 15/00 | (2006.01) |
| A61B 5/11 | (2006.01) |
| A61B 5/103 | (2006.01) |
| G01C 22/00 | (2006.01) |

(52) U.S. Cl.
CPC ............... *A61B 5/112* (2013.01); *A61B 5/1038* (2013.01); *G01C 22/006* (2013.01)

(58) Field of Classification Search
USPC ................................................. 702/141, 160
See application file for complete search history.

(56) References Cited

U.S. PATENT DOCUMENTS

| | | | |
|---|---|---|---|
| 2004/0094613 A1* | 5/2004 | Shiratori et al. | ............. 235/105 |
| 2006/0211956 A1* | 9/2006 | Sankai | ............................ 601/5 |
| 2009/0227424 A1* | 9/2009 | Hirata et al. | ...................... 482/7 |

FOREIGN PATENT DOCUMENTS

| | | |
|---|---|---|
| EP | 2 005 887 A1 | 12/2008 |
| JP | A-2001-218754 | 8/2001 |
| JP | A-2002-336376 | 11/2002 |
| JP | A-2005-352686 | 12/2005 |
| JP | A-2008-109966 | 5/2008 |
| JP | A-2008-229266 | 10/2008 |
| JP | A-2009-000391 | 1/2009 |
| JP | A-2009-106377 | 5/2009 |
| JP | A-2009-106387 | 5/2009 |

OTHER PUBLICATIONS

Nov. 9, 2010 International Search Report issued in International Patent Application No. PCT/JP2010/067365 (with translation).

* cited by examiner

*Primary Examiner* — Mohamed Charioui
(74) *Attorney, Agent, or Firm* — Oliff PLC

(57) ABSTRACT

A walking posture determination apparatus correlates detected acceleration of a subject with walking posture. The apparatus stores an association between walking posture levels and values of an index that represents walking posture, calculates the index value by using acceleration that is detected by an acceleration sensor, and determines the walking posture level based on the calculated index value.

18 Claims, 25 Drawing Sheets

Left foot acceleration    Right foot acceleration

Left foot acceleration    Right foot acceleration

| Level | | Acceleration (right foot − left foot) | Acceleration ratio |
|---|---|---|---|
| Left | −5 | −0.05 | −1.5 |
| | −4 | −0.04 | −1.2 |
| | −3 | −0.03 | −0.9 |
| | −2 | −0.02 | −0.6 |
| Normal | −1 | −0.01 | −0.3 |
| | 0 | 0 | 0 |
| | 1 | 0.01 | 0.3 |
| Right | 2 | 0.02 | 0.6 |
| | 3 | 0.03 | 0.9 |
| | 4 | 0.04 | 1.2 |
| | 5 | 0.05 | 1.5 |

FIG. 13

| Level | | Acceleration average value |
|---|---|---|
| Left | −5 | 0.05 |
| | −4 | 0.04 |
| | −3 | 0.03 |
| | −2 | 0.02 |
| Normal | −1 | 0.01 |
| | 0 | 0 |
| | 1 | −0.01 |
| Right | 2 | −0.02 |
| | 3 | −0.03 |
| | 4 | −0.04 |
| | 5 | −0.05 |

FIG. 17

| Level | | Acceleration |
|---|---|---|
| Narrow | -5 | 0 |
| | -4 | 0.02 |
| | -3 | 0.04 |
| | -2 | 0.06 |
| Normal | -1 | 0.08 |
| | 0 | 0.1 |
| | 1 | 0.12 |
| Wide | 2 | 0.14 |
| | 3 | 0.16 |
| | 4 | 0.18 |
| | 5 | 0.2 |

FIG. 20

|  |  | Stride length | | |
|---|---|---|---|---|
|  |  | High | Middle | Low |
| Stride width | High | High-intensity walking | Bow-legged | Unstable walking |
|  | Middle | High-intensity walking | Normal | Energy-saving walking |
|  | Low | Catwalking | Catwalking | Unstable walking |

WALKING POSTURE DETERMINATION APPARATUS

This is a Continuation of International Application No. PCT/JP2010/067365 filed Oct. 4, 2010, which claims the benefit of Japanese Application No. JP2009-232673 filed Oct. 6, 2009. The disclosure of the prior applications is hereby incorporated by reference herein in its entirety.

TECHNICAL FIELD

This disclosure relates to a determination apparatus for determining a walking posture.

BACKGROUND ART

Balance and symmetry are critical elements in the evaluation of posture beauty.

As technology for evaluating posture during walking, JP 2001-218754A discloses technology for evaluating the beauty and health of movement by analyzing foot pressure distribution during walking. Also, JP 2008-109966A discloses technology for creating a Lissajous figure for an acceleration waveform and displaying the distribution of the acceleration of the center of gravity of a body. For example, when time variation in the forward-backward or left-right acceleration of a measurement subject is expressed, an ideal walking posture with uniform left-right balance is represented by a line graph such as that shown in FIG. 23A. When time variation in the forward-backward acceleration of a measurement subject is expressed, a walking posture in which the stride length of the right foot is long is represented by a line graph such as that shown in FIG. 23B, in which the forward-backward acceleration is high in the right foot walking period. When time variation in the left-right acceleration of a measurement subject is expressed, a walking posture in which the center of gravity is right-of-center is represented by a line graph such as that shown in FIG. 24A, in which there is a large degree of variation in acceleration on the right side in the right foot walking period. When time variation in the forward-backward acceleration of a measurement subject is expressed, a so-called "bow-legged" walking posture in which the stride width is greatly shifted left and right is represented by a line graph such as that shown in FIG. 24B, in which there is a small degree of variation in forward-backward acceleration in the walking period of one foot (the right foot in this figure).

SUMMARY OF INVENTION

However, such conventional technology requires large-scale equipment for measurement. Also, in such conventional technology, the environment (e.g., the place) in which measurement can be performed is limited. Furthermore, content displayed in such technology generally requires specialized knowledge to be understood, and cannot be universally understood in real-time. For example, specialized knowledge is required to understand the walking posture represented by the line graphs shown in FIGS. 23A to 24B. Accordingly, it can be difficult to evaluate walking posture in daily life as well as give improvement guidance for and make corrections to walking posture using such technology.

Aspects of this disclosure have been achieved in light of such conventional technology, and one object of this disclosure is to provide a walking posture determination apparatus that can determine a walking posture easily and in real-time.

According to one aspect of the present invention, there is provided a walking posture determination apparatus that includes: a main body unit; an acceleration sensor for detecting acceleration of the main body unit; a storage unit for storing associations between walking posture levels and index values of an index representing a walking posture; a calculation unit for calculating an index value of the index representing a walking posture using first-direction acceleration detected by the acceleration sensor, and determining a walking posture level to which the calculated index value belongs; and an output unit for outputting, as a walking posture determination result, the walking posture level determined by the calculation unit.

The index representing a walking posture can be at least one of stride length, center-of-gravity balance, and stride width.

The storage unit can store associations between walking posture levels and index values of a plurality of indices representing a walking posture, and associations between types of walking postures and combinations of walking posture levels or index values of the plurality of indices representing a walking posture, the calculation unit determines a type of walking posture in accordance with the calculated index value, and the output unit displays the type of walking posture determined by the calculation unit as the walking posture determination result.

The calculation unit can determine a walking posture level for each of a plurality of indices representing a walking posture, and the output unit displays, on a screen, the walking posture levels determined by the calculation unit using a single graph whose axes respectively indicate the indices.

As the walking posture determination result, the output unit can display the walking posture level on a screen using a bubble chart in which a position or a size are in accordance with the determined walking posture level.

The walking posture determination apparatus can further include an input unit for accepting input of a walking posture level as a target level, and the calculation unit calculates a difference between the determined walking posture level and the input walking posture level, and the output unit furthermore outputs the difference calculated by the calculation unit.

The output unit can perform at least one of output using a display screen, output using a vibrating apparatus, output using light, and output using audio.

The index representing a walking posture can be stride length, as walking posture levels regarding stride length, the storage unit stores levels of balance between a stride length in a left foot walking interval and a stride length in a right foot walking interval, in association with the index values, the calculation unit performs calculation for, using the first-direction acceleration, extracting acceleration in the right foot walking interval and acceleration in the left foot walking interval from second-direction acceleration of the main body unit, performs calculation for calculating, as the index value, a difference or ratio between the acceleration in the right foot walking interval and the acceleration in the left foot walking interval, and determines a level of balance between the stride length in the left foot walking interval and the stride length in the right foot walking interval to which the calculated index value belongs, and as the walking posture determination result, the output unit outputs the level of balance between the stride length in the left foot walking interval and the stride length in the right foot walking interval that was determined by the calculation unit.

The index representing a walking posture can be center-of-gravity balance, as walking posture levels regarding center-of-gravity balance, the storage unit stores levels of balance between right-side center of gravity and left-side center of gravity, in association with the index values, the calculation unit performs calculation for calculating, as the index value, an average value of the first-direction acceleration in a predetermined period, and determines a level of balance between the right-side center of gravity and the left-side center of gravity to which the calculated index value belongs, and as the walking posture determination result, the output unit outputs the level of balance between the right-side center of gravity and the left-side center of gravity that was determined by the calculation unit.

The index representing a walking posture can be stride width, as walking posture levels regarding stride width, the storage unit stores levels of stride width magnitude, in association with the index values, the calculation unit performs calculation for calculating, as the index value, an amplitude of variation in the first-direction acceleration, and determines a level of stride width magnitude to which the calculated index value belongs, and as the walking posture determination result, the output unit outputs the level of stride width magnitude that was determined by the calculation unit.

In accordance with one aspect of the invention, the walking posture determination apparatus enables determining a walking posture easily and in real-time without requiring a large-scale apparatus. Also, visually displaying determination results can facilitate an understanding of the determination results without having specialized knowledge, and further allows easy communication of improvement guidance for and making corrections to walking posture.

BRIEF DESCRIPTION OF DRAWINGS

FIG. 13 is a diagram showing a specific example of a center of gravity determination table.

FIG. 17 is a diagram showing a specific example of a stride width determination table.

FIG. 20 is a diagram illustrating a display of walking posture determination results.

DETAILED DESCRIPTION OF EMBODIMENTS

The following describes an embodiment of the present invention with reference to the drawings. In the following description, parts and constituent elements that are the same will be given the same reference signs. The names and functions thereof are also the same.

In the present embodiment, a determination apparatus for determining a walking posture is realized as a pedometer. However, the apparatus realizing the walking posture determination apparatus is not limited to being a pedometer, and may be any apparatus that can detect later-described variation in acceleration that accompanies the walking of a measurement subject. One example is a system configured by a detection apparatus for detecting variation in acceleration and a processing apparatus (e.g., a computer) connected thereto for processing the detection results of the detection apparatus.

Figure 1A:
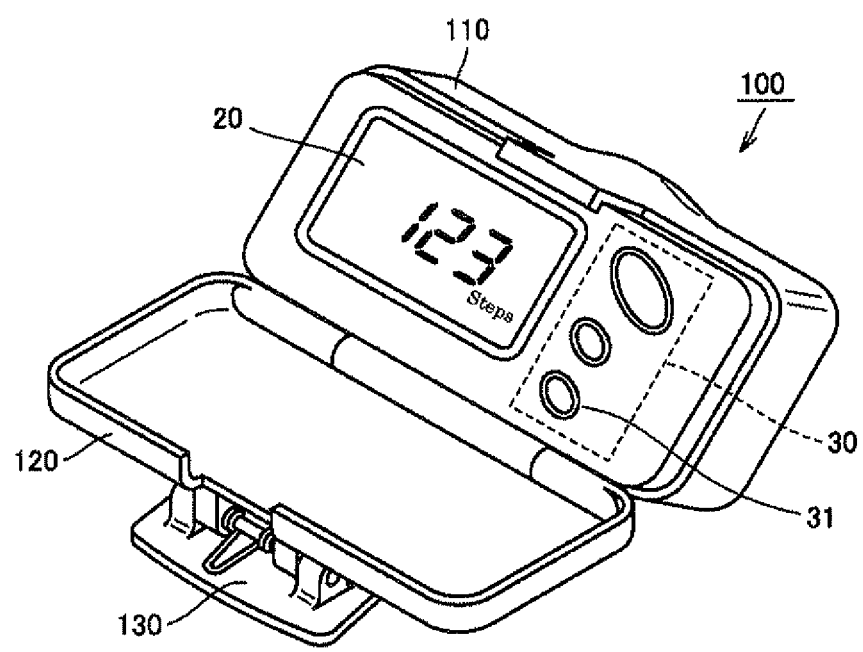
FIG. 1A is a diagram showing a specific example of the appearance of a pedometer according to an embodiment.

As shown in FIG. 1A, a pedometer 100 according to the present embodiment has a small main body casing that is portable, and the main body casing is divided into a case body 110, a cover body 120, and a clip body 130.

The case body 110 has a display face that is provided with a display 20 that can display various types of information such as the counted number of steps and number of calories burned and buttons 30 for accepting user operations. Among the buttons 30 is a determination button 31 for instructing the start of walking posture determination operations that will be described later.

Figure 1B:
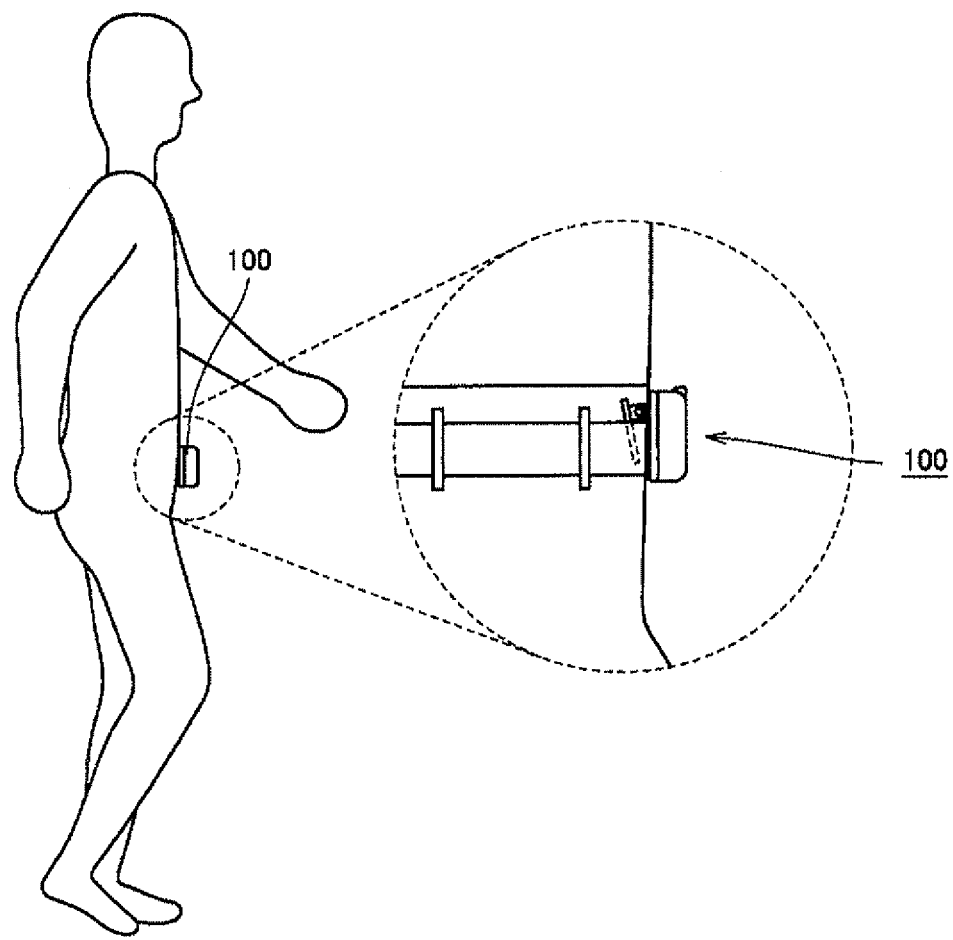
FIG. 1B is a diagram showing a specific example of the wearing of the pedometer according to an embodiment.

The lower edge of the case body 110 and the cover body 120 are coupled such that the junction portion can rotate about an axis, and the pedometer 100 is opened and closed by rotation of the junction portion. The clip body 130 is provided on the face of the cover body 120 that is on the opposite side of the face opposing the display face of the case body 110. As shown in FIG. 1B, the clip body 130 enables the pedometer 100 to be worn in the vicinity of the user's second sacrum segment, the user's left/right lumbar region, or the like.

Figure 2:
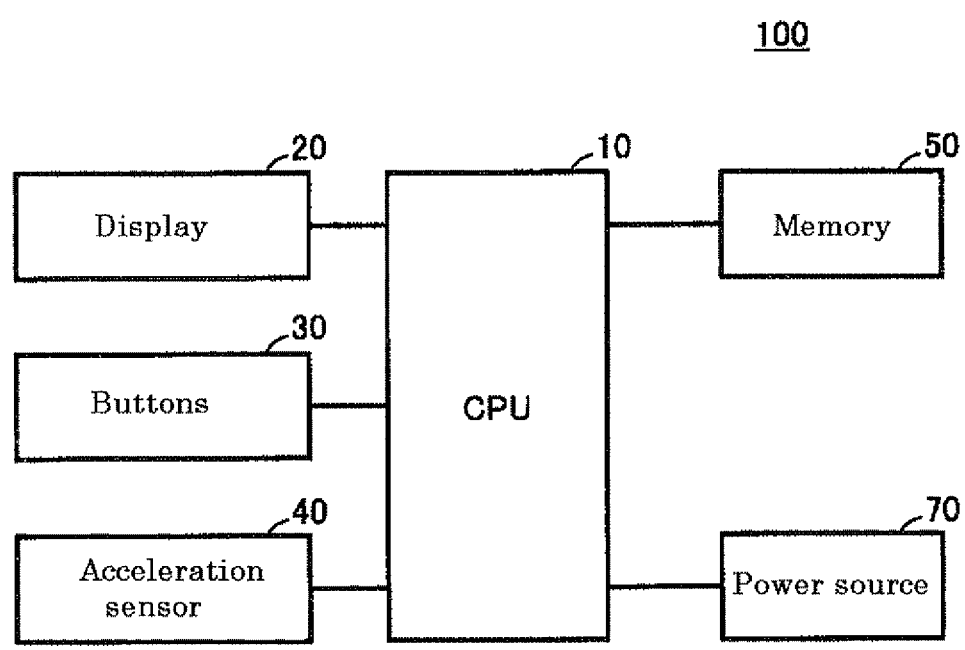
FIG. 2 is a diagram showing a specific example of a hardware configuration of the pedometer according to an embodiment.

As shown in FIG. 2, in one example of the hardware configuration of the pedometer 100, the pedometer 100 includes a CPU (Central Processing Unit) 10 for performing overall control, the above-described display 20 and buttons 30, an acceleration sensor 40, a memory 50 for storing, for example, a program executed by the CPU 10, and a power source 70 such as a battery. The acceleration sensor 40 includes two sensors provided at an angle that enables measurement of acceleration in at least two later-described directions among three orthogonal axis directions, in order to obtain acceleration data to be used in later-described determination processing. Note that the acceleration sensor 40 is a sensor that detects variation in acceleration in various axis directions in order to detect body movement, and this sensor is not limited to being an acceleration sensor as long as it is a sensor that similarly detects body movement. For example, a gyroscope, magnetic sensor, or the like that detects acceleration in various directions may be installed in place of the acceleration sensor 40.

Figure 3:
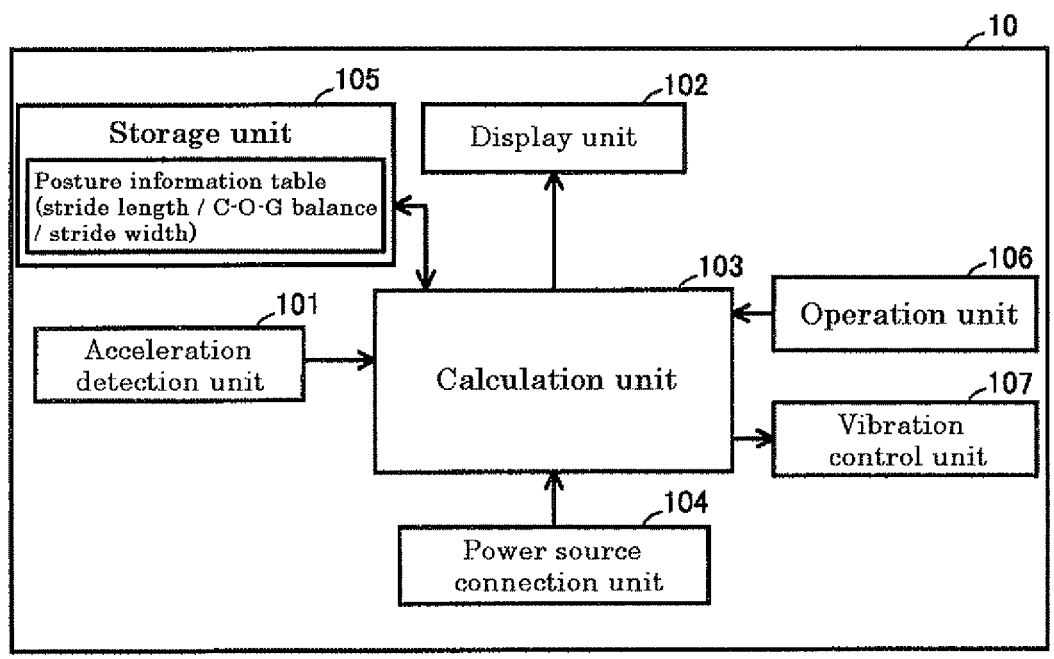
FIG. 3 is a diagram showing a specific example of a functional configuration of the pedometer according to an embodiment.

As shown in FIG. 3, in one example of the configuration of the pedometer 100, the pedometer 100 includes an acceleration detection unit 101 for detecting acceleration based on input from the acceleration sensor 40, a display unit 102 for controlling the display on the display 20, a calculation unit 103 for performing acceleration calculation and calculation in later-described posture determination, a power source connection unit 104 for performing processing for connecting to the power source 70 and supplying power to the overall apparatus, a storage unit 105 for storing, for example, determination results and later-described posture information tables used in the calculation performed by the calculation unit 103, and an operation unit 106 for accepting input of operation signals from the buttons 30 and inputting necessary signals to the calculation unit 103. The functions of these units may be realized in the CPU 10 by the CPU 10 reading out and executing a program stored in the memory 50, and the functions of at least a portion of these units may be configured by hardware such as electrical circuits.

The calculation unit 103 determines that the measurement subject has made a walking movement using the acceleration detected by the acceleration detection unit 101 and a threshold value stored in advance, and counts the number of steps. The calculation unit 103 furthermore calculates a measurement subject movement amount using the height and stride length of the measurement subject, which are stored in the storage unit 105 or the like in advance. The movement amount corresponds to a travel amount (travel distance), burned calories, or the like. Also, as the movement amount, the calculation unit 103 can calculate later-described movement amounts of the measurement subject in various directions.

Figure 4:
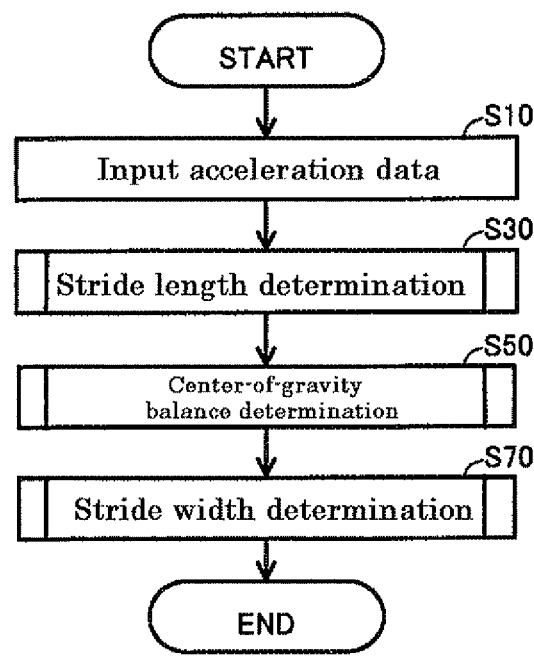
FIG. 4 is a flowchart showing a flow of walking posture determination operations performed by the pedometer according to an embodiment.

The calculation unit 103 also performs calculation for determining a walking posture. The following describes a flow of walking posture determination operations performed by the pedometer 100 with reference to FIG. 4. The operations shown in FIG. 4 are started when the operation unit 106 receives an operation signal from the determination button 31 due to the determination button 31 being pressed. Also, these operations may be automatically started when the calculation unit 103 detects body movement and the measurement of the number of steps is to be performed.

As shown in FIG. 4, the calculation unit 103 of the pedometer 100 accepts an input of acceleration data from the acceleration detection unit 101 (step (hereinafter abbreviated as "S") 10), and makes a stride length determination (S30), a center-of-gravity balance determination (S50), and a stride width determination (S70) as walking posture index determinations made using the acceleration data, thus calculating respective indices. Each determination result may be displayed after the corresponding determination has been made, or the determination results may be collectively displayed after all of the determinations have been made.

The walking posture determination operations shown in FIG. 4 are performed repeatedly. These operations then end when, for example, the operation unit 106 again receives an operation signal from the determination button 31, that is to say, when an operation for ending the determination operations has been detected. Also, these operations may automatically end when body movement is no longer detected by the calculation unit 103.

Next is a detailed description of operations in the stride length determination (S30), the center-of-gravity balance determination (S50), and the stride width determination (S70).

Figure 5:
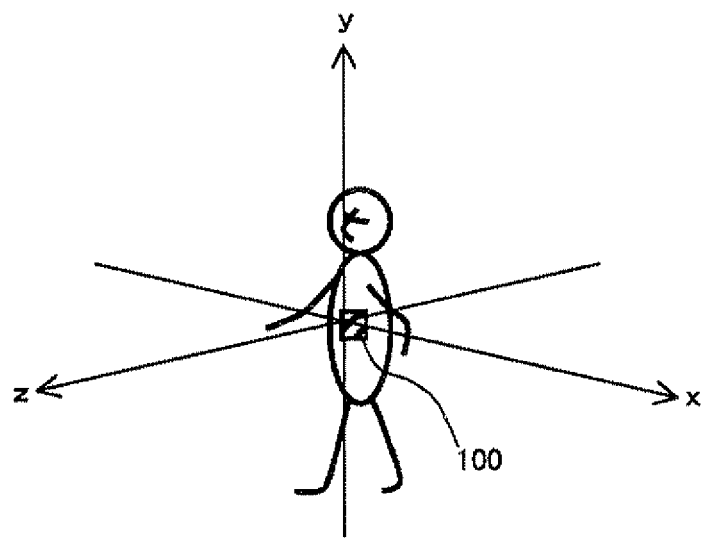
FIG. 5 is a diagram illustrating directions of acceleration measured by the pedometer.

First, the acceleration data input in S10 will be described with reference to FIG. 5. In the pedometer 100, the measurement performed by the acceleration sensor 40 results in the input of acceleration in at least two directions as shown in FIG. 5, namely x-axis acceleration as horizontal-axis acceleration of the measurement subject and y-axis acceleration as vertical-axis acceleration of the measurement subject. Out of such acceleration data, the calculation unit 103 makes the stride length determination using the y-axis acceleration data, makes the center-of-gravity balance determination using the x-axis acceleration data, and makes the stride width determination using the x-axis acceleration data.

Note that although the calculation unit 103 performs calculation for determining a walking posture using the acceleration data as indices representing body movement in the following example, the walking posture determination may be made using a movement amount such as a travel distance or burned calories calculated based on acceleration. In such a case well, calculation can be performed similarly to the calculation described below.

Figure 6:
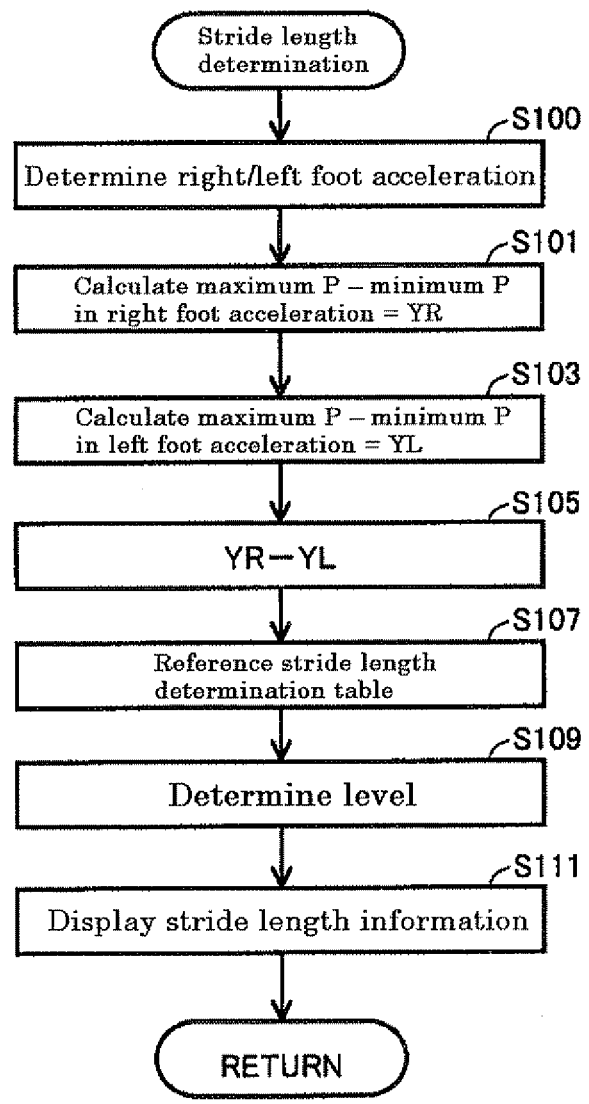
FIG. 6 is a flowchart showing a flow of stride length determination performed in S30 of FIG. 4.

As shown in FIG. 6, in the stride length determination of S30, the calculation unit 103 determines acceleration in a right foot walking period and acceleration in a left foot walking period in the vertical-axis (y-axis) acceleration data in S100. Here, the walking period for one foot (i.e., the walking period for one step) is the period from touchdown of the heel of that one foot to the next touchdown of that heel.

Right-side acceleration in the horizontal-axis (x-axis) acceleration is largest in the right foot walking period, and left-side acceleration in the horizontal-axis (x-axis) acceleration is largest in the left foot walking period. In the variation in acceleration represented by the solid line in FIG. 7, right-side acceleration is represented as positive, and left-side acceleration is represented as negative, and therefore the period of upwardly protruding variation in acceleration represents the right foot walking period, and the period of downwardly protruding variation in acceleration represents the left foot walking period.

As for the vertical-axis (y-axis) acceleration, acceleration varies in the walking period for one foot as follows: the acceleration gradually rises from 0 and reaches a maximum value, then gradually falls to 0 and farther down to a minimum value, and thereafter again gradually rises back to 0. In the variation in acceleration represented by the broken line in FIG. 7, increasing acceleration is represented as positive, and decreasing acceleration is represented as negative, and therefore one set of an upwardly protruding period and a downwardly protruding period represents the walking period for one foot (i.e., the walking period for one step).

Figure 7:
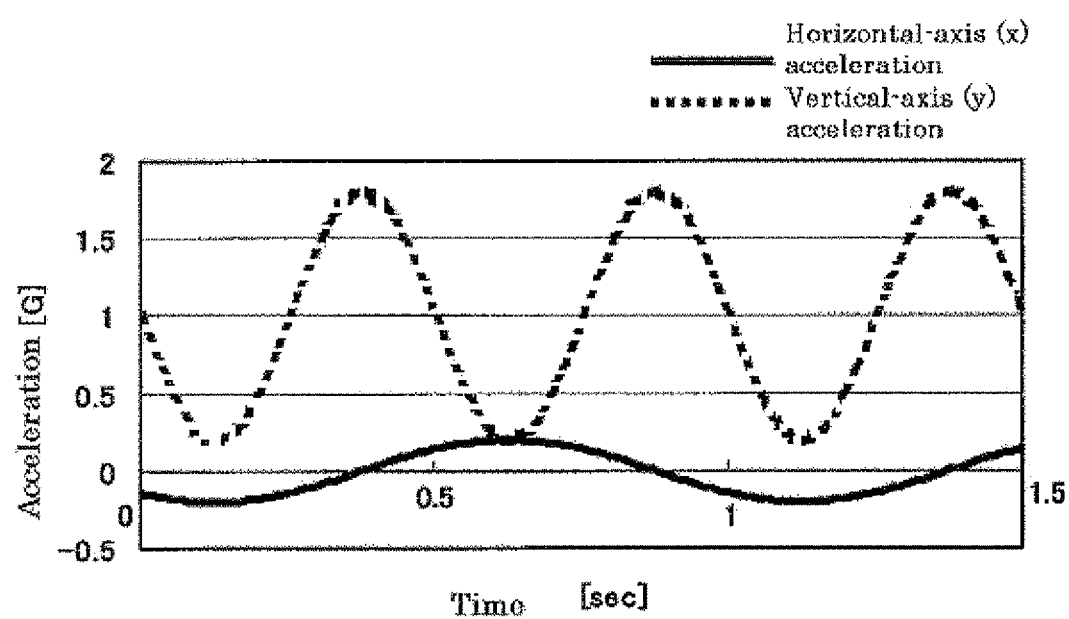
FIG. 7 is a diagram showing a specific example of acceleration data that is input.

In view of this, as shown in FIG. 7, in S100 the calculation unit 103 superimposes one period of horizontal-axis acceleration data on one period of vertical-axis acceleration data in synchronization with the measurement time thereof, and thereby determines whether periods of variation in vertical-axis acceleration represent variation in vertical-axis acceleration in the right foot walking period or represents variation in vertical-axis acceleration in the left foot walking period, and extracts acceleration for respective periods from the horizontal-axis acceleration data.

The calculation unit 103 calculates a maximum amplitude YR of the vertical-axis (y-axis) acceleration in the right foot walking period calculated in S100 (the difference between the maximum value and minimum value of the period of variation in acceleration (the same follows hereinafter)), and a maximum amplitude YL of the vertical-axis (y-axis) acceleration in the left foot walking period (S101 and S103). Then, in determining the stride length serving as an index, the calculation unit 103 calculates the difference YR−YL between the maximum amplitude YR and the maximum amplitude YL, or the ratio YR/YL thereof as an index value (S105).

Figure 8A:
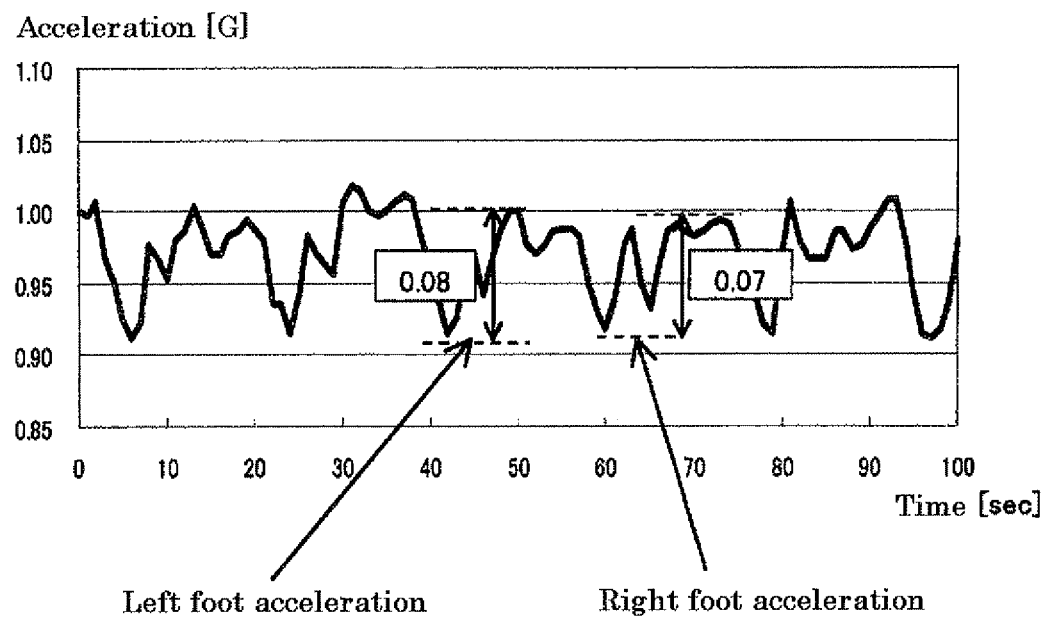
FIG. 8A is a diagram showing a specific example of vertical-axis acceleration data at a certain stride length level.
Figure 8B:
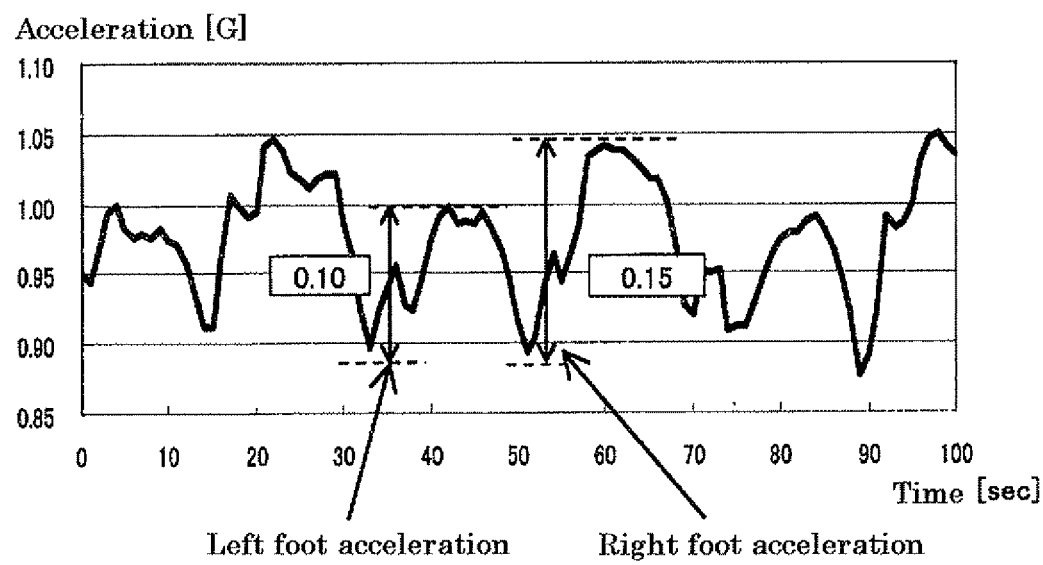
FIG. 8B is a diagram showing a specific example of vertical-axis acceleration data at another stride length level.
Figures 9, 10:
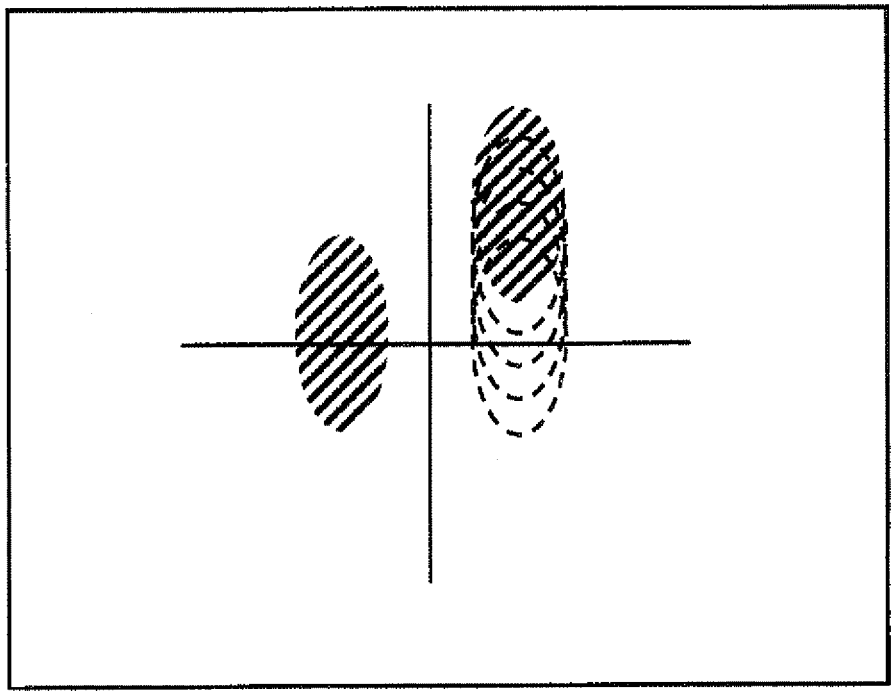
FIG. 9 is a diagram showing a specific example of a stride length determination table.
FIG. 10 is a diagram showing a specific example of a display of stride length determination results.

As shown in FIG. 8A, in the case where the left and right stride lengths are substantially equal, and the stride length levels are normal levels, a large difference is not seen between the maximum amplitude YR and the maximum amplitude YL. On the other hand, in the case where the stride length of the right foot is longer than the stride length of the left foot as shown in FIG. 8B for example, the maximum amplitude YR in the right foot walking period is greater than the maximum amplitude YL in the left foot walking period. In view of this, the storage unit 105 stores, as a posture information table, a stride length determination table specifying associations between stride length levels and relationships between left and right amplitudes during walking, as shown in FIG. 9. Specifically, the stride length determination table in FIG. 9 specifies the relationships between stride length levels and differences between the maximum amplitude YR and the maximum amplitude YL, and the relationships between stride length levels and ratios between the maximum amplitude YR and the maximum amplitude YL. Either of these relationships with stride length levels may be specified, or both of these relationships with stride length levels may be specified. In FIG. 9, the value of the stride length level is greater the more the right foot stride length is greater than the left foot stride length, the value of the stride length level is 0 when the stride lengths are equal, and the value of the stride length level is smaller the more the left foot stride length is greater than the right food stride length.

Note that although the stride length determination table shown in FIG. 9 is stored in the storage unit 105 in advance, the stride length determination table may be able to be changed by a predetermined operation performed using the buttons 30. Also, the stride length determination table may be corrected based on user information that is input in advance and stored in the storage unit 105, examples of which include the height and gender of the measurement subject. The same follows for later-described tables used in other determinations.

Also, the stride length determination table in FIG. 9 is used when the calculation unit 103 performs calculation for making a stride length determination using acceleration as an index representing body movement. As described above, in the case where travel distance is used as an index representing body movement in the calculation performed by the calculation unit 103, the stride length determination table specifies, for example, associations that stride length levels have with differences between a reference travel distance and left and right foot travel distances, or ratios between a reference travel distance and left and right foot travel distances. Examples of the travel distance used as a reference here include a stride length or value calculated based on the height of the measurement subject stored in the storage unit 105 in advance (e.g., the value being height—100 cm), or a value stored in advance.

In S107, the calculation unit 103 references the stride length determination table, and in S109, the calculation unit 103 determines the stride length level of the measurement subject to be the stride length level specified by the difference YR−YL or the ratio YR/YL, which is the index value calculated in S105.

In the case shown in FIG. 8A, the difference between the maximum amplitude YR and the maximum amplitude YL is calculated to be −0.01 [G], and therefore the stride length level is determined in S109 to be −1, which indicates a normal level. On the other hand, in the case shown in FIG. 8B, the difference between the maximum amplitude YR and the maximum amplitude YL is calculated to be 0.05 [G], and therefore the stride length level is determined in S109 to be +5, which indicates that the right foot stride length is long.

Based on the determination results obtained by the calculation unit 103, in S111 the display unit 102 performs processing for displaying the determination results on the display 20. Here, processing is performed for displaying the bubble chart shown in FIG. 10 representing the shape of feet, where a foot is displayed higher as the stride length increases. Specifically, the display unit 102 stores the association between stride length levels and display positions in advance, and determines the display position in accordance with the determination results obtained in S109 and causes the determined display position to be displayed differently from other display positions. Displaying the bubble chart shown in FIG. 10 makes it possible for even a user lacking specialized knowledge to intuitively grasp which foot's stride length is longer (or shorter) than the other foot's stride length, and by how much.

Figure 11:
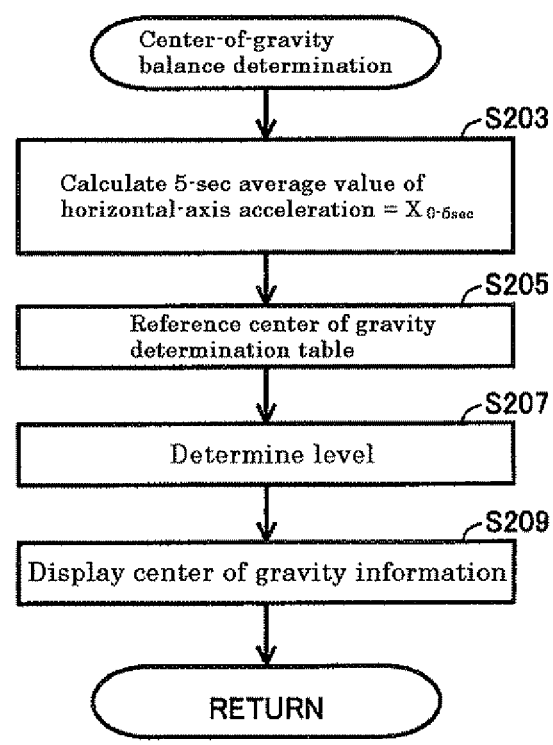
FIG. 11 is a flowchart showing a flow of center-of-gravity balance determination performed in S50 of FIG. 4.

Next, as shown in FIG. 11, the calculation unit 103 determines a center-of-gravity balance serving as an index in the center-of-gravity balance determination of S50, and in this determination, the calculation unit 103 calculates, as the index value, an average value $X_{0-5sec}$ of horizontal-axis (x-axis) acceleration for a predetermined time (e.g., five seconds) (S203).

Figure 12A:
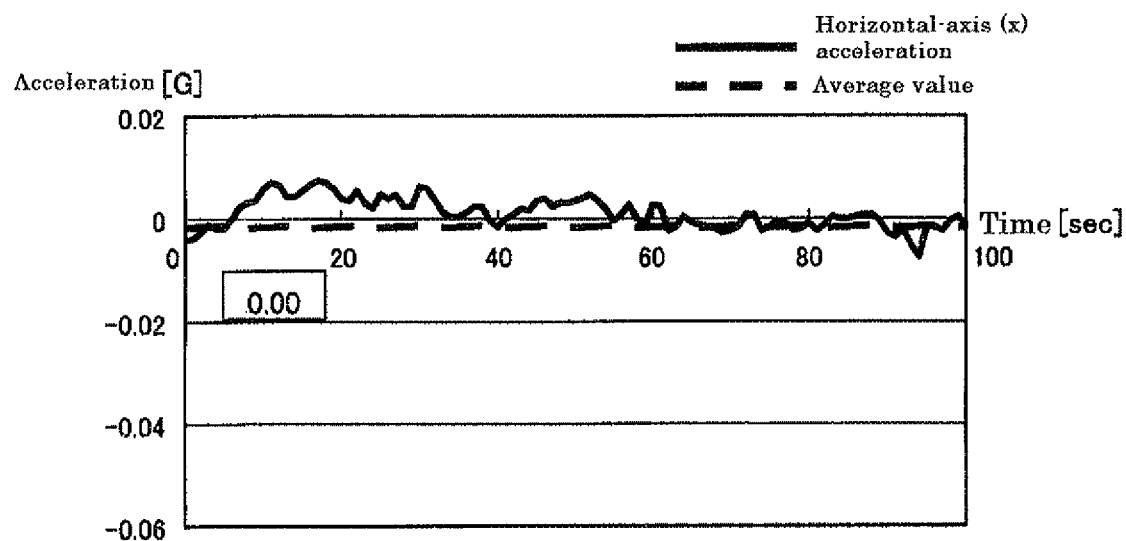
FIG. 12A is a diagram showing a specific example of horizontal-axis acceleration data at a certain center-of-gravity balance level.
Figure 12B:
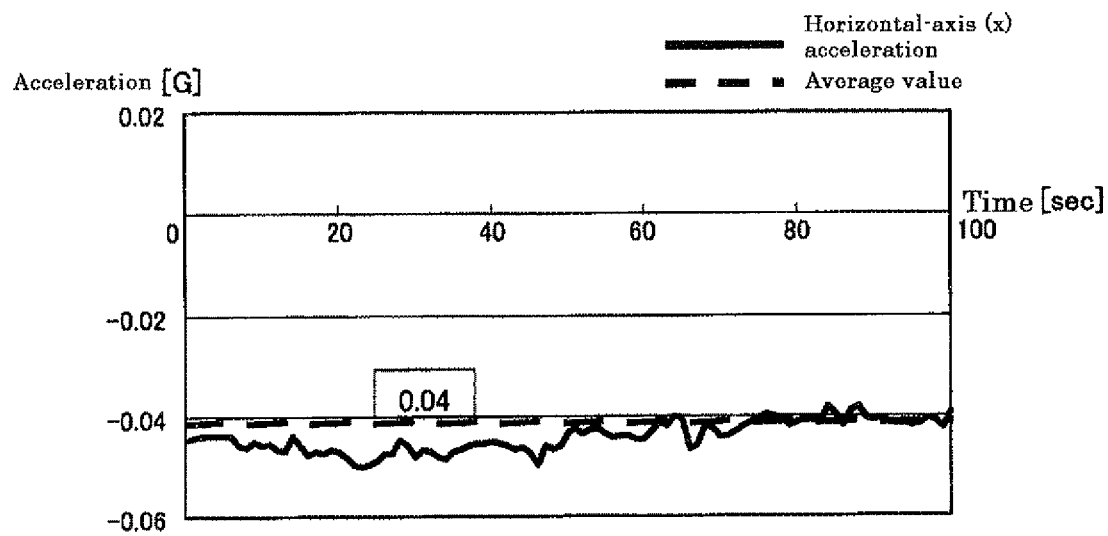
FIG. 12B is a diagram showing a specific example of horizontal-axis acceleration data at another center-of-gravity balance level.

As shown in FIG. 12A, in the case where the left and right centers of gravity are substantially equal, and the left and right center-of-gravity balance levels are normal levels, the average value $X_{0-5sec}$ of horizontal-axis (x-axis) acceleration is substantially 0 [G], and it can be said that the variations in left and right acceleration during walking are substantially the same. On the other hand, in the case where the center of gravity is skewed to the right as shown in FIG. 12B for example, the average value $X_{0-5\ sec}$ of horizontal-axis (x-axis) acceleration is a negative value, which indicates that the right-side acceleration is larger. In view of this, the storage unit 105 stores, as a posture information table, a center of gravity determination table specifying associations between center-of-gravity levels and average values $X_{0-5sec}$ of horizontal-axis (x-axis) acceleration during walking as shown in FIG. 13. In FIG. 13, the value of the center-of-gravity level is greater the greater the center-of-gravity is skewed to the left, the value of the center-of-gravity level is 0 when the left and right centers of gravity are substantially the same, and the value of the center-of-gravity level is smaller the greater the center-of-gravity is skewed to the right.

In S205, the calculation unit 103 references the center of gravity determination table, and in S207, the calculation unit 103 determines the center-of-gravity level of the measurement subject to be the center-of-gravity level specified by the average value $X_{0-5sec}$, which is the index value calculated in S203.

In the case shown in FIG. 12A, the average value $X_{0-5sec}$ is calculated to be 0.00 [G], and therefore the center-of-gravity level is determined in S207 to be 0, which indicates a normal level. On the other hand, in the case shown in FIG. 12B, the average value $X_{0-5sec}$ is calculated to be −0.04 [G], and therefore the center-of-gravity level is determined in S207 to be +4, which indicates that the center of gravity is skewed to the right.

Note that it is assumed that the pedometer 100 is worn by the measurement subject at the center in the horizontal axis direction (e.g., the position of the navel), and the center of gravity determination table shown in FIG. 13 specifies center-of-gravity levels based on left and right skewing from that position. For this reason, a configuration is possible in which the storage unit 105 furthermore stores left and right center of gravity determination tables that specify center-of-gravity levels based on left and right skewing taking the wearing position into consideration in the case where the measurement subject wears the pedometer 100 on the left side (e.g., the left hip) or the right side (e.g., the right hip), and the calculation unit 103 selects the center of gravity determination table that is to be used in accordance with an operation such as the pressing of a button (not shown) included among the buttons 30 for instructing the wearing position. Also, a configuration is possible in which the calculation unit 103 corrects the center of gravity determination table shown in FIG. 13 in accordance with the wearing position and uses the corrected table in the center-of-gravity balance determination, in accordance with an operation such as the pressing of a button (not shown) included among the buttons 30 for instructing the wearing position.

Figure 14:
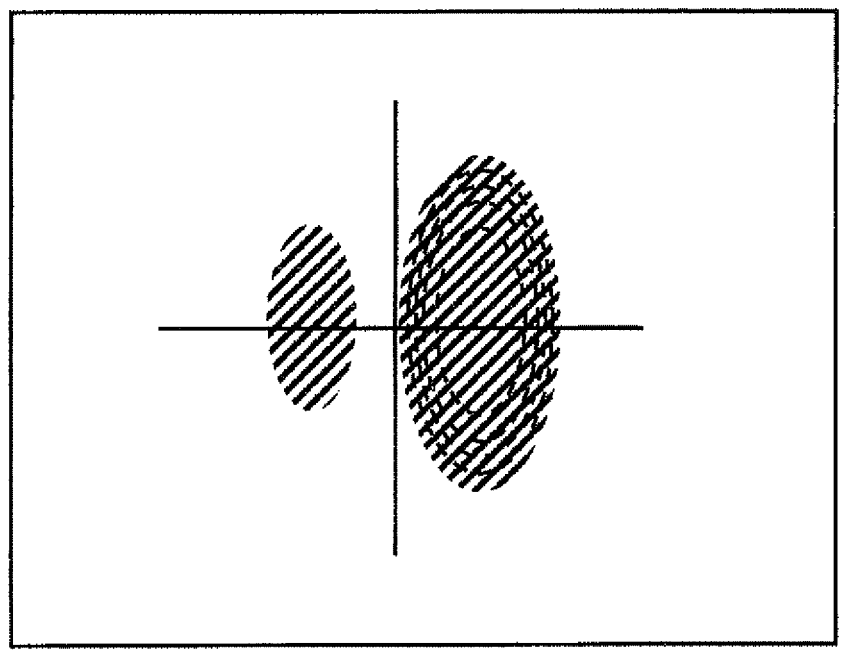
FIG. 14 is a diagram showing a specific example of a display of center-of-gravity balance determination results.

Based on the determination results obtained by the calculation unit 103, in S209 the display unit 102 performs processing for displaying the determination results on the display 20. Here, processing is performed for displaying the bubble chart shown in FIG. 14 representing the shape of feet, where the more the center of gravity is skewed, the larger the displayed size of the foot is. Specifically, the display unit 102 stores the association between center-of-gravity levels and display sizes in advance, and determines a display size in accordance with the determination results obtained in S207 and causes the foot shape on the corresponding side to be displayed at the determined size. Displaying the bubble chart shown in FIG. 14 makes it possible for even a user lacking specialized knowledge to intuitively grasp which foot's center of gravity is skewed more (or less) than the other foot's center of gravity, and by how much.

Figure 15:
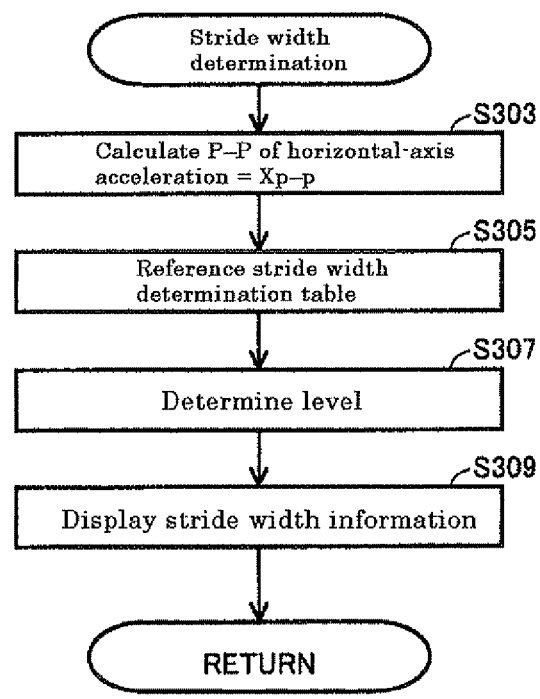
FIG. 15 is a flowchart showing a flow of stride width determination performed in S70 of FIG. 4.

Next, as shown in FIG. 15, the calculation unit 103 determines a stride width serving as an index in the stride width determination of S70, and in this determination, the calculation unit 103 calculates, as the index value, a difference Xp–p between the maximum value and minimum value of horizontal-axis (x-axis) acceleration in one period of variation in acceleration (S303).

Figure 16A:
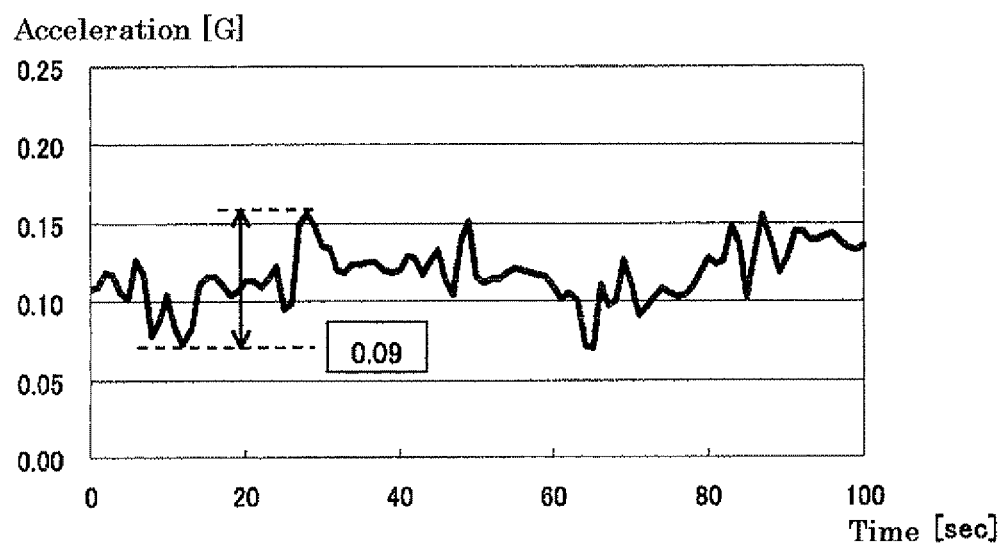
FIG. 16A is a diagram showing a specific example of horizontal-axis acceleration data at a certain stride width level.
Figure 16B:
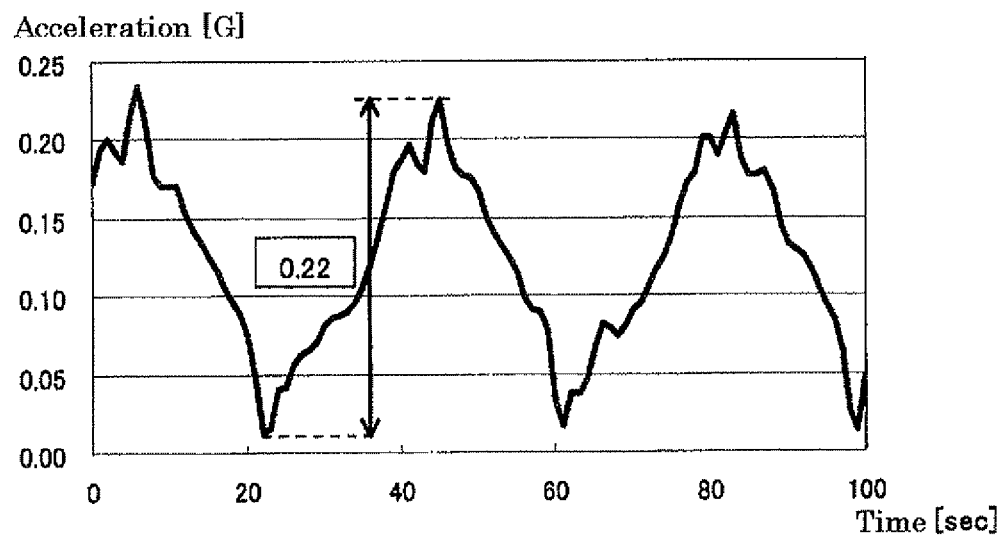
FIG. 16B is a diagram showing a specific example of horizontal-axis acceleration data at another stride width level.

As shown in FIG. 16A, in the case where the stride width is a normal level of about shoulder width for example, the difference Xp–p obtained from the horizontal-axis (x-axis) acceleration data is approximately in the range of 0.08 to 0.12 [G]. On the other hand, as shown in FIG. 16B, in the case where the stride width is a level higher than the normal stride width assumed to be shoulder width for example, the variation in left and right acceleration is large (i.e., is greatly shifted to the left and right) in one period of variation in acceleration corresponding to a walking period made up of a pair of a left foot walking period and a right foot walking period, and therefore the difference Xp–p obtained from the horizontal-axis (x-axis) acceleration data is greater than 0.14 [G]. In view of this, the storage unit 105 stores, as a posture information table, a stride width determination table specifying associations between stride width levels and differences Xp–p between the maximum value and minimum value of acceleration in one period of variation in horizontal-axis (x-axis) acceleration during walking, as shown in FIG. 17. In FIG. 17, the stride width level is greater the greater the stride width is, and the stride width level approaches the value of 0 as the stride width approaches a normal width such as an ordinary shoulder width.

In S305, the calculation unit 103 references the stride width determination table, and in S307, the calculation unit 103 determines the stride width level of the measurement subject to be the stride width level specified by the difference Xp–p, which is the index value calculated in S303.

In the case shown in FIG. 16A, the difference Xp–p is calculated to be 0.09 [G], and therefore the stride width level is determined in S307 to be −1, which indicates a normal level. On the other hand, in the case shown in FIG. 16B, the difference Xp–p is calculated to be 0.22 [G], and therefore the stride width level is determined in S307 to be +5, which indicates that the stride width is large.

Note that with the stride width determination shown in FIG. 17 as well, it is assumed that the pedometer 100 is worn by the measurement subject at the center in the horizontal axis direction (e.g., the position of the navel), and therefore similarly to the center of gravity determination table in FIG. 13, stride width determination tables respectively for the cases where the pedometer 100 is worn on the left side and the right side of the measurement subject may be stored, or the stride width determination table may be corrected in accordance with the wearing position.

Figure 18:
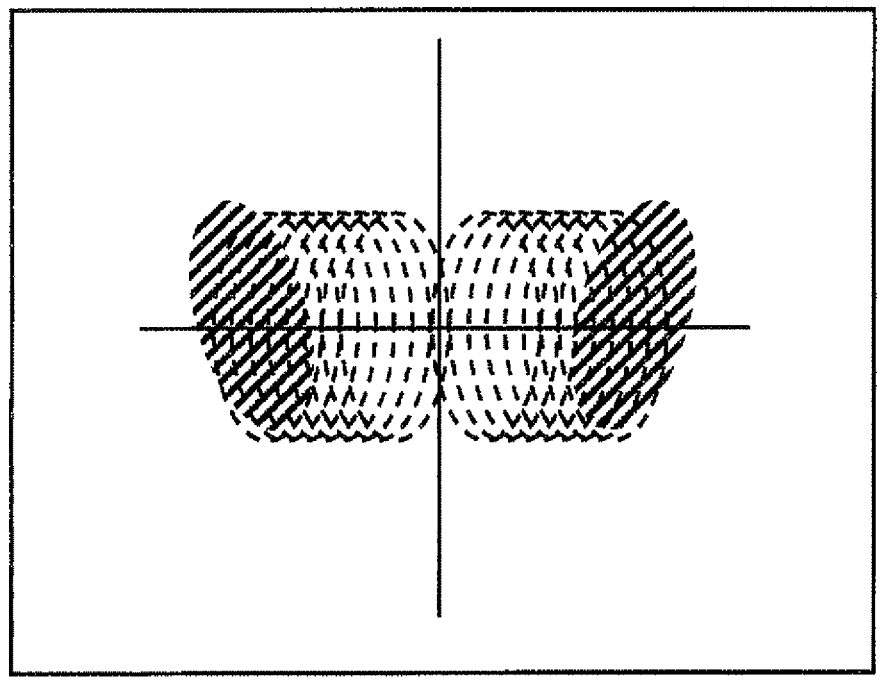
FIG. 18 is a diagram showing a specific example of a display of stride width determination results.

Based on the determination results obtained by the calculation unit 103, in S309 the display unit 102 performs processing for displaying the determination results on the display 20. Here, processing is performed for displaying the bubble chart shown in FIG. 18 representing the shape of feet, where the gap between foot shapes is in accordance with the magnitude of the stride width. Specifically, the display unit 102 stores the association between stride width levels and display positions (foot shape gaps) in advance, and determines a display gap in accordance with the determination results obtained in S307 and causes the left and right foot shapes to be displayed with the determined gap. Displaying the bubble chart shown in FIG. 18 makes it possible for even a user lacking specialized knowledge to intuitively grasp how large the stride width is.

Performing the above-described determination operations in the pedometer 100 enables obtaining walking posture determination results without using a large-scale apparatus. Also, since the determination operations are performed in the pedometer 100 at the time of walking and measurement, it is possible to obtain walking posture determination results in real-time. Furthermore, displaying the determination results using bubble charts representing the shape of feet as shown in FIGS. 10, 14, and 18 enables even a user lacking specialized knowledge to intuitively grasp the determination results and easily make a walking posture evaluation. This enables easily giving the measurement subject walking posture improvement guidance and making corrections for bringing the measurement subject's walking posture closer to an ideal walking posture.

Variation 1

In the determination operations shown in FIGS. 4, 6, 11, and 15, the determination results are displayed after the corresponding determinations are made in the pedometer 100. However, in place of such displaying, or in addition to such displaying, a configuration is possible in which after the stride length determination of S30, the center-of-gravity balance determination of S50, and the stride width determination of S70, at least two results from among the determination results of these determinations are collectively displayed.

For example, the following describes the case of displaying the results of the stride length determination and the results of the center-of-gravity balance determination after the aforementioned determination operations have been performed. Here, the display unit 102 can read out, from the calculation unit 103, the stride length level determined in S109 and the center-of-gravity level determined in S207, and display a bar graph such as that shown in FIG. 19A or a level display such as that shown in FIG. 19B, in which the stride length level is indicated by the vertical axis and the center-of-gravity level is indicated by the horizontal axis. In the case where the results of the stride length determination, the results of the center-of-gravity balance determination, and the results of the stride width determination are all to be displayed, the display unit 102 can display each of the determination results using a three-dimensional graph. Preferably, the display unit 102 can change the display range based on the determination results. Specifically, it is preferable that the display unit 102 determines a display range in which the level determined as a determination result by the calculation unit 103 is in the vicinity of the maximum value, and generates display data using the determined display range.

Figure 19A:
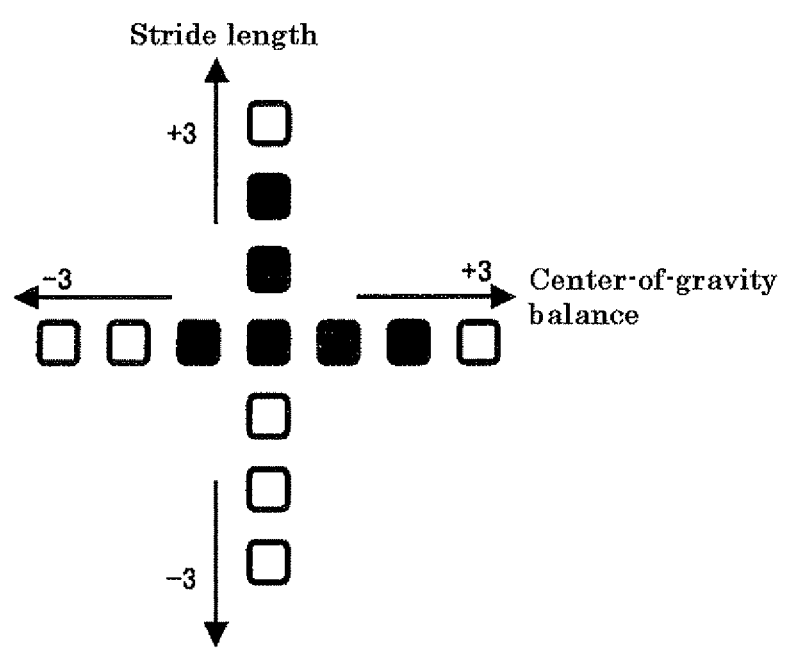
FIG. 19A is a diagram showing a specific example of a display of walking posture determination results.
Figure 19B:
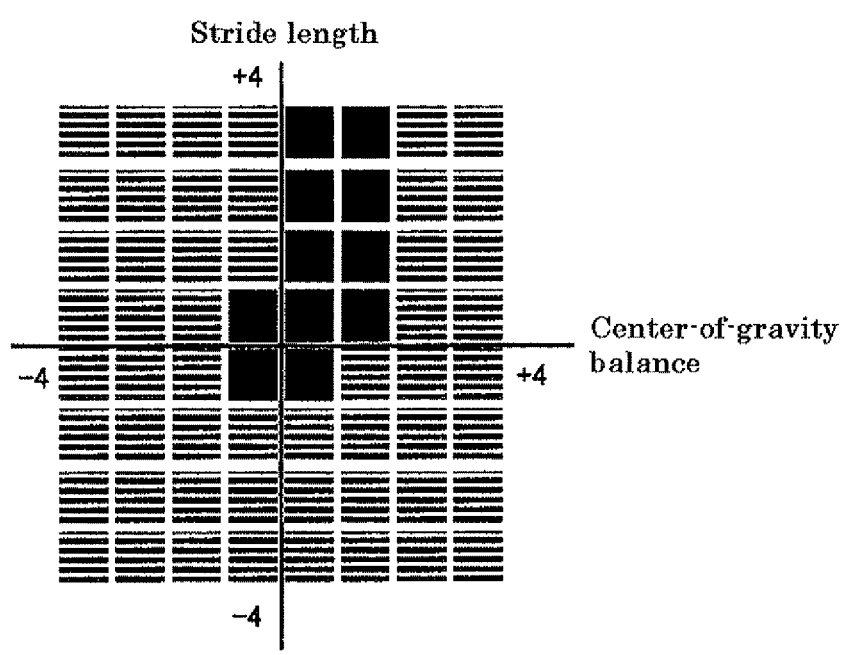
FIG. 19B is a diagram showing a specific example of a display of walking posture determination results.

Based on the display shown in FIG. 19A, it is possible to intuitively grasp that the walking posture is a walking posture in which the stride length level is +3 and the center-of-gravity balance is +2, that is to say, the right foot stride length is long, and the center of gravity of the left foot is skewed. Also, based on the display shown in FIG. 19B, it is possible to intuitively grasp that the walking posture is a walking posture in which the stride length level is +4 and the center-of-gravity balance is +2, that is to say, the right foot stride length is long, and the center of gravity of the left foot is skewed.

Alternatively, a configuration is possible in which the storage unit 105 furthermore stores associations between types of walking postures and at least two determination results from among those of the stride length determination, the center-of-gravity balance determination, and the stride width determination as shown in FIG. 20, and the calculation unit 103 determines the type of walking posture based on the determination results after the above determinations have been made. FIG. 20 shows an example of storing associations between types of walking postures and ranges (high, middle, and low) to which the levels obtained as determination results belong. However, associations between types of walking postures and levels obtained as determination results may be stored, or associations between types of walking postures and index values obtained as determination results may be stored. In such cases as well, it is possible to determine and display the type of walking posture similarly to the following example.

For example, as shown in FIG. 20, if the result of the stride length determination and the result of the stride width determination respectively indicate a stride length level associated with a high stride length and a stride width level associated with a middle to high stride width, the calculation unit 103 determines that the type of walking posture is "high-intensity walking". Also, if the stride length level is associated with a middle stride length, and the stride width level is associated with a high stride width, the calculation unit 103 determines that the type of walking posture is "bow-legged". Also, if the stride length level is associated with a low stride length, and the stride width level is associated with a high or low stride width, the calculation unit 103 determines that the type of walking posture is "unstable walking". Also, if the stride length level is associated with a middle to high stride length, and the stride width level is associated with a low stride width, the calculation unit 103 determines that the type of walking posture is "catwalking (model walking)". Also, if the stride length level is associated with a middle stride length, and the stride width level is associated with a middle stride width, the calculation unit 103 determines that the type of walking posture is "normal". When the walking posture determination is made, the display unit 102 displays the type of walking posture on the display 20 after the various determinations have been made. The type of walking posture may be displayed along with the walking posture determination results.

Determining the type of walking posture and displaying the type of walking posture in this way enables the walking posture to be grasped more intuitively.

Variation 2

In the determination operations shown in FIGS. 4, 6, 11, and 15, the pedometer 100 references the stored posture information tables and obtains, as a determination result, the level specified as being associated with a measurement value in the table. As another example, a configuration is possible in which target levels are set in advance as an ideal walking posture, and differences from such levels are displayed. In this case, the operation unit 106 accepts an input of target levels given by operating the buttons 30, and inputs the target levels to the calculation unit 103. Alternatively, a configuration is possible in which target walking style selections (model walking, high exercise efficiency walking, and the like) are displayed on the display 20, the operation unit 106 accepts a selection made via the buttons 30, and the calculation unit 103 references associations that have been stored in advance and sets target levels in accordance with the selected walking style.

Figure 21A:
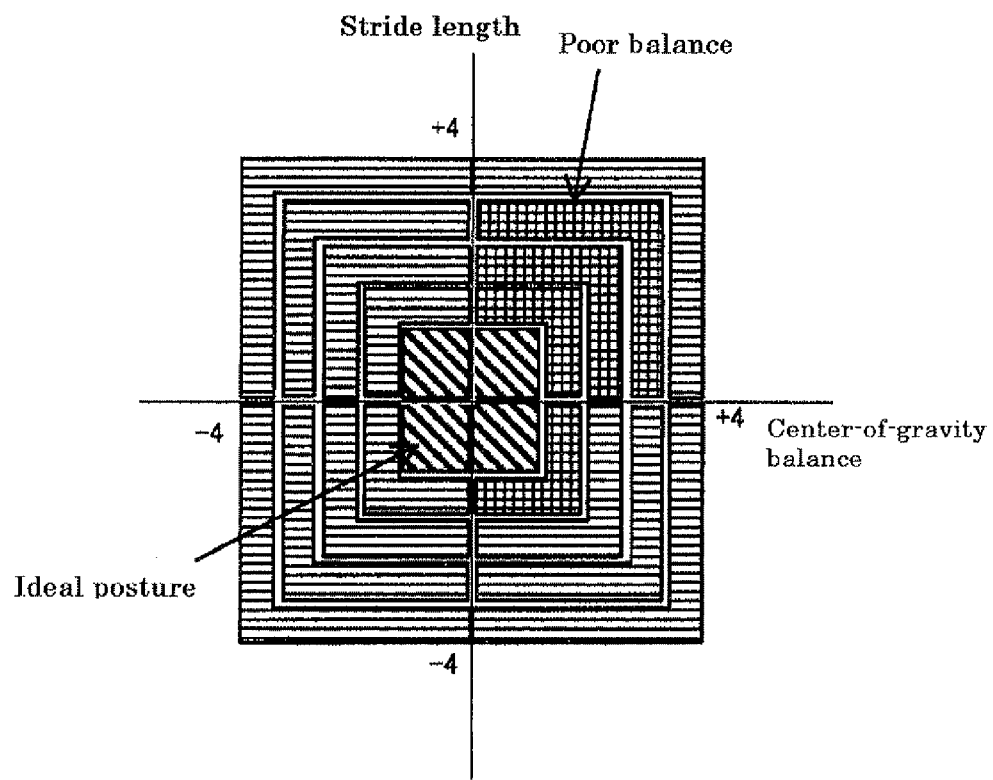
FIG. 21A is a diagram showing another example of output of walking posture determination results.

As the differences between the levels determined in the above-described determination operations and the input target levels, the calculation unit 103 calculates differences from the index values (horizontal-axis acceleration, vertical-axis acceleration, or the like) that were used in the determinations. In place of or in addition to displaying a bubble chart such as that shown in FIG. 10, the display unit 102 displays the differences from the target levels that were calculated by the calculation unit 103, as shown in FIG. 21A. In place of a display such as that shown in FIG. 21A, a bubble chart representing the shape of feet may be displayed similarly to the case of the above-described determination results (levels).

This enables the user to intuitively become aware of differences between the target walking posture and the actual walking posture, and can easily provide walking posture improvement guidance and suggest corrections for bringing the walking posture closer to an ideal walking posture.

Also, a configuration is possible in which the pedometer 100 is connected to vibrating apparatuses, and differences from target levels that have been calculated by the calculation unit 103 are alerted by vibration of the vibrating apparatuses.

Figure 21B:
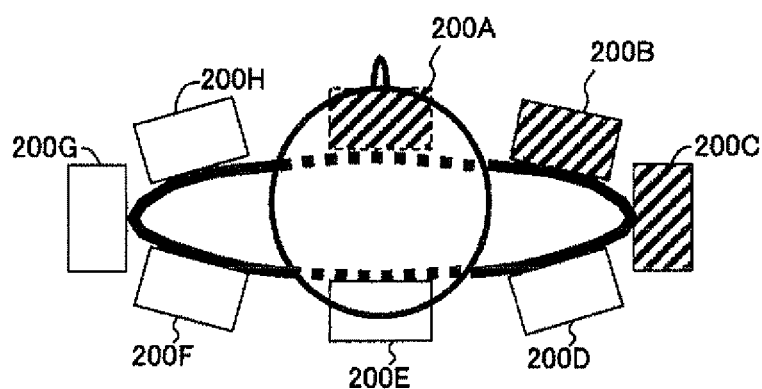
FIG. 21B is a diagram illustrating wearing positions of vibrating apparatuses.

As a specific example, the pedometer 100 is connected to vibrating apparatuses 200A to 200H. As shown in FIG. 21B, these vibrating apparatus are worn at specified positions around a portion of the body where it is easy to be conscious of walking, such as the measurement subject's waist. Specifically, as shown in FIG. 21B, the vibrating apparatuses 200A to 200H are worn positioned with substantially equal gaps therebetween in the stated order starting from the center of the front side of the measurement subject (e.g., from the position of the navel) and moving substantially horizontally to the right. In this case, the pedometer 100 includes a vibration control unit 107 for controlling the vibrating of the vibrating apparatus 200A to 200H, as shown in FIG. 3.

Associations between differences from target levels, a vibrating apparatus among the vibrating apparatuses 200A to 200H that is to be caused to vibrate, and the degree of vibration are stored in the vibration control unit 107 in advance. For example, degrees of vibration can be associated with corresponding differences from a target level such that degrees of vibration for the vibrating apparatus 200A worn in the center of the front side of the measurement subject and the vibrating apparatus 200E worn in the center of the back side of the measurement subject are associated with differences from a target level in the stride length determination, the vibrating apparatus 200A is caused to vibrate if the right foot stride length is greater than the target level, and the vibrating apparatus 200E is caused to vibrate if the left foot stride length is greater than the target level, for example. As another example, degrees of vibration can be associated with corresponding differences from a target level such that degrees of vibration for the vibrating apparatus 200C worn on the right side of the measurement subject and the vibrating apparatus 200G worn on the left side of the measurement subject are associated with differences from target levels in the center-of-gravity balance determination and the stride width determination, the vibrating apparatus 200C is caused to vibrate if the center of gravity is more skewed to the right than the target level or the right foot stride width is greater than the target level, and the vibrating apparatus 200G is caused to vibrate if the center of gravity is more skewed to the left than the target level or the left foot stride width is greater than the target level, for example. As a further example, degrees of vibration for the vibrating apparatuses 200B, 200D, 200F, and 200H that are worn between the left, right, front center, and back center of the measurement subject can be associated with differences from target levels in at least two determinations among the stride length determination, the center-of-gravity balance determination, and the stride width determination, and the vibrating apparatuses positioned at the various locations in accordance with the determinations can be caused to vibrate with degrees of vibration in accordance with the differences from the target levels.

In this way, alerting a difference from a target level by vibration of a vibrating apparatus enables the measurement subject to sense a determination result without viewing the display 20 during walking, and make corrections so as to bring the walking posture closer to an ideal walking posture.

Figure 22:
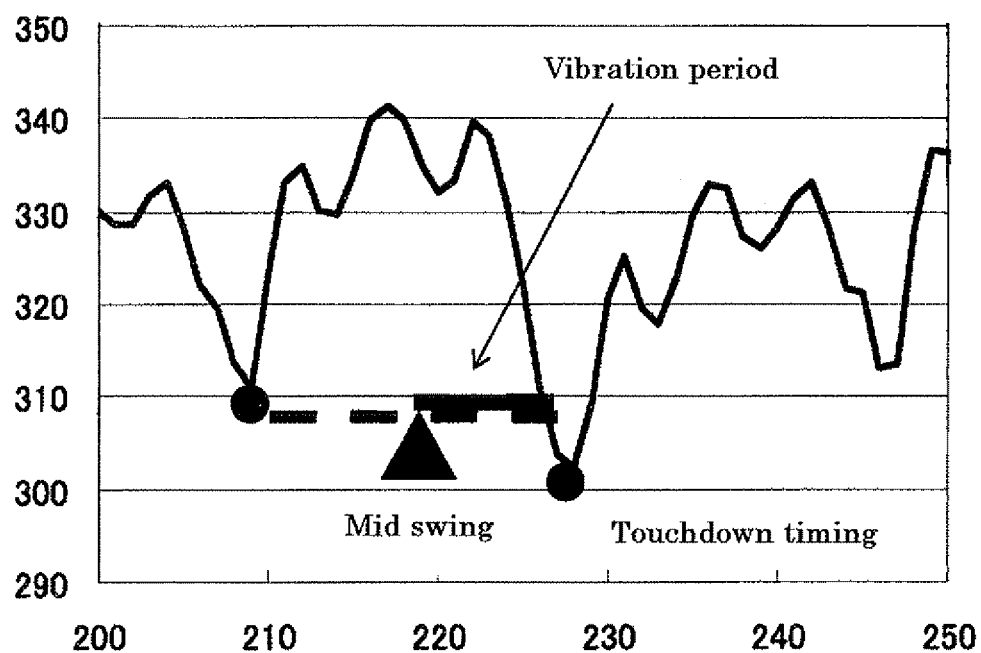
FIG. 22 is a diagram illustrating vibrating timings of the vibrating apparatuses.
Figure 23A:
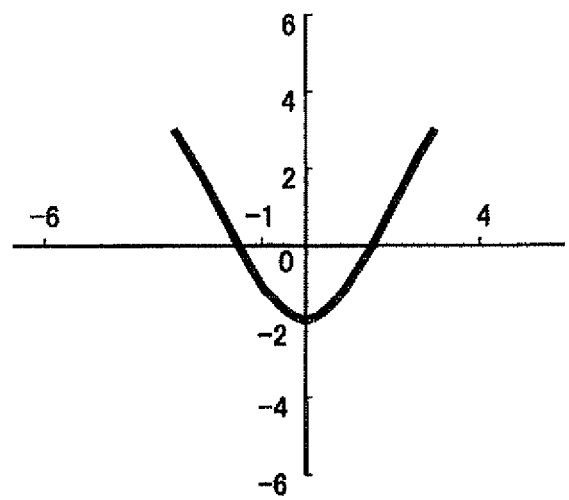
FIG. 23A is a diagram illustrating a conventional method of displaying walking posture determination results.
Figure 23B:
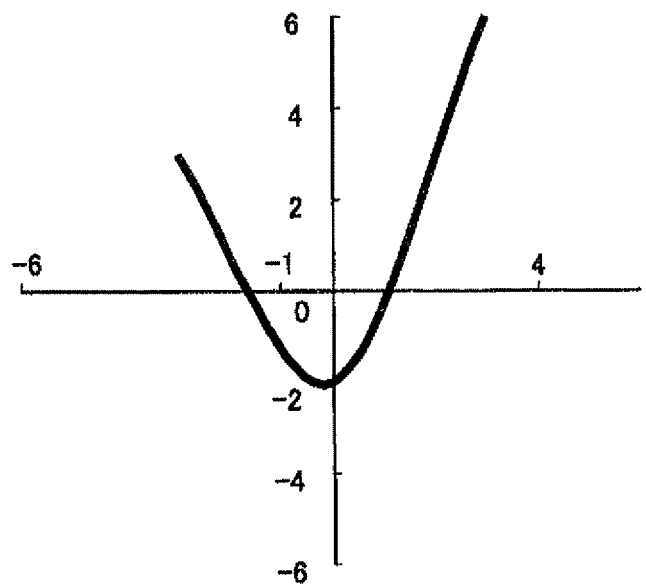
FIG. 23B is a diagram illustrating a conventional method of displaying walking posture determination results.
Figure 24A:
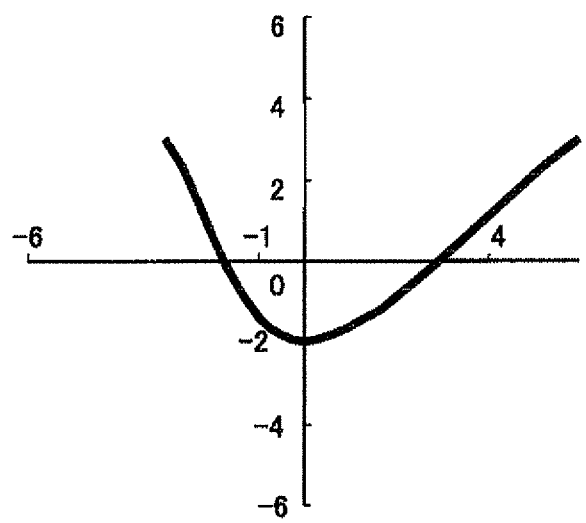
FIG. 24A is a diagram illustrating a conventional method of displaying walking posture determination results.
Figure 24B:
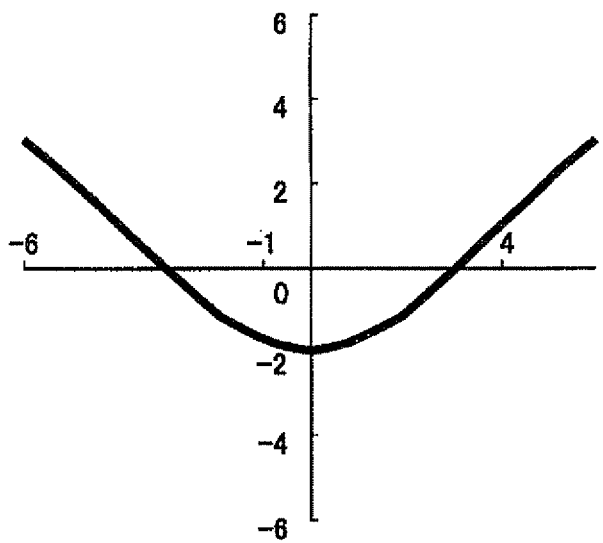
FIG. 24B is a diagram illustrating a conventional method of displaying walking posture determination results.

Note that it is preferable that the vibration control unit 107 performs control so as to cause the vibrating apparatuses to vibrate in a predetermined period within the walking period of one foot. Specifically, as shown in FIG. 22, the vibration control unit 107 performs control so as to cause the vibrating apparatuses to vibrate in a period from the approximate middle of the walking period for one foot (i.e., the period from touchdown of the heel of one foot until the next touchdown of that heel) until the next touchdown. Vibration timing can be controlled by calculating the approximate middle of the walking period for one foot based on the vertical-axis acceleration data in a walking period that is at least prior to the walking period in which the vibrating apparatuses are to be caused to vibrate, and storing the calculated approximate middle in the vibration control unit 107.

Although differences from target levels are alerted using a display screen on the display 20 or vibration of the vibrating apparatuses in the second variation, alerting may be similarly performed using a light output apparatus, an audio output apparatus, or the like, or a combination of such output apparatuses. Furthermore, determination results may be output in a similar manner.

Furthermore, it is possible to provide a program for causing a computer to execute the determination operations described above. The computer may be installed in the pedometer 100, and a configuration is possible in which the computer is connected to the pedometer 100 and performs the determination operations upon receiving data indicating an index representing body movement, such as acceleration data, from the pedometer 100.

Such a program can be provided as a program product recorded on a computer-readable recording medium with which a computer is supplied, such as a flexible disk, a CD-ROM (Compact Disk-Read Only Memory), a ROM (Read Only Memory), a RAM (Random Access Memory), or a memory card. Alternatively, the program can be provided recorded on a recording medium built into a computer, such as a hard disk. Moreover, the program can be provided by downloading via a network.

Note that the program of the present invention may invoke necessary modules, among program modules provided as part of a computer operating system (OS), in a predetermined sequence at predetermined timings, and cause such modules to execute processing. In this case, processing is executed in cooperation with the OS, without the above modules being included in the program itself. Such a program that does not include modules can also be the program of the present invention.

Also, the program of the present invention may be provided incorporated in part of another program. In this case as well, processing is executed in cooperation with the other program, without the modules included in the other program being included in the program itself. Such a program incorporated in another program can also be the program of the present invention.

The program product that is provided is executed after being installed in a program storage unit such as a hard disk. Note that the program product includes the program itself and the recording medium on which the program is recorded.

The embodiments of the invention described above are to be considered in all respects only as illustrative and not restrictive. The scope of the invention is indicated by the appended claims rather than the above description, and all changes which come within the meaning and range of equivalency of the claims are to be embraced within the scope of the invention.

The invention claimed is:
1. A walking posture determination apparatus comprising:
a main body;
an acceleration sensor configured to detect an acceleration of the main body;
a storage device configured to store: (i) associations between walking posture levels and index values of an index representing a walking posture, the index representing the walking posture being stride length, and (ii) levels of balance between a stride length in a left foot walking interval and a stride length in a right foot walking interval, in association with the index values, the levels of balance being stored as walking posture levels regarding stride length; and a processor programmed to:
calculate an index value of the index representing the walking posture based on at least a first-direction acceleration detected by the acceleration sensor,
determine a walking posture level to which the calculated index value corresponds,
perform calculation for extracting an acceleration in the right foot walking interval based on the first-direction acceleration of the main body,
perform calculation for extracting an acceleration in the left foot walking interval based on a second-direction acceleration of the main body,
calculate, as the index value, a difference or ratio between the acceleration in the right foot walking interval and the acceleration in the left foot walking interval,
determine a level of balance between the stride length in the left foot walking interval and the stride length in the right foot walking interval to which the calculated index value corresponds, and
output, as a walking posture determination result, the determined walking posture level, the walking posture determination result being the determined level of balance between the stride length in the left foot walking interval and the stride length in the right foot walking interval.

2. The walking posture determination apparatus according to claim 1, wherein
the storage device stores associations between walking posture levels and index values of a plurality of indices representing walking posture, and stores associations between types of walking postures and combinations of walking posture levels or index values of the plurality of indices representing walking posture, and
the processor is programmed to:
determine a type of walking posture in accordance with the calculated index value, and
display the type of walking posture determined as the walking posture determination result.

3. The walking posture determination apparatus according to claim 1, wherein the processor is programmed to:
determine the walking posture level for each of a plurality of indices representing walking posture, and
display, on a screen, the determined walking posture levels using a single graph whose axes respectively indicate the indices.

4. The walking posture determination apparatus according to claim 1, wherein the processor is programmed to display the walking posture level on a screen, as the walking posture determination result, using a bubble chart in which a position or a size of a displayed graphic are selected based on the determined walking posture level.

5. The walking posture determination apparatus according to claim 1, wherein the processor is programmed to:
accept input of a walking posture level as a target level,
calculate a difference between the determined walking posture level and the input walking posture level, and
output the calculated difference.

6. The walking posture determination apparatus according to claim 1, wherein the processor is programmed to perform at least one of output using a display screen, output using a vibrating apparatus, output using light, and output using audio.

7. A walking posture determination apparatus comprising:
a main body;
an acceleration sensor configured to detect an acceleration of the main body;
a storage device configured to store: (i) associations between walking posture levels and index values of an index representing a walking posture, the index representing is the walking posture being center-of-gravity balance, and (ii) levels of balance between a right-side center of gravity and a left-side center of gravity, in association with the index values, the levels of balance being stored as walking posture levels regarding center-of-gravity balance; and
a processor programmed to:
calculate an index value of the index representing the walking posture based on at least a first-direction acceleration detected by the acceleration sensor,
determine a walking posture level to which the calculated index value corresponds,
calculate, as the index value, an average value of the first-direction acceleration in a predetermined period,
determine a level of balance between the right-side center of gravity and the left-side center of gravity to which the calculated index value corresponds,
output, as a walking posture determination result, the determined walking posture level, and
output, as the walking posture determination result, the determined level of balance between the right-side center of gravity and the left-side center of gravity.

8. The walking posture determination apparatus according to claim 7, wherein
the storage device stores associations between walking posture levels and index values of a plurality of indices representing walking posture, and stores associations between types of walking postures and combinations of walking posture levels or index values of the plurality of indices representing walking posture, and
the processor is programmed to:
determine a type of walking posture in accordance with the calculated index value, and
display the type of walking posture determined as the walking posture determination result.

9. The walking posture determination apparatus according to claim 7, wherein the processor is programmed to:
determine the walking posture level for each of a plurality of indices representing walking posture, and
display, on a screen, the determined walking posture levels using a single graph whose axes respectively indicate the indices.

10. The walking posture determination apparatus according to claim 7, wherein the processor is programmed to display the walking posture level on a screen, as the walking posture determination result, using a bubble chart in which a position or a size of a displayed graphic are selected based on the determined walking posture level.

11. The walking posture determination apparatus according to claim 7, wherein the processor is programmed to:
accept input of a walking posture level as a target level,
calculate a difference between the determined walking posture level and the input walking posture level, and
output the calculated difference.

12. The walking posture determination apparatus according to claim 7, wherein the processor is programmed to perform at least one of output using a display screen, output using a vibrating apparatus, output using light, and output using audio.

13. A walking posture determination apparatus comprising:
a main body;
an acceleration sensor configured to detect an acceleration of the main body;
a storage device configured to store: (i) associations between walking posture levels and index values of an index representing a walking posture, the index representing walking posture being stride width, and (ii) levels of stride width magnitude in association with the index values, the levels of stride width being stored as walking posture levels regarding stride width; and
a processor programmed to:
calculate an index value of the index representing a walking posture based on at least a first-direction acceleration detected by the acceleration sensor,
determine a walking posture level to which the calculated index value corresponds,
calculate, as the index value, an amplitude of variation in the first-direction acceleration,
determine a level of stride width magnitude to which the calculated index value corresponds,
output, as a walking posture determination result, the determined walking posture level, and
output, as the walking posture determination result, the determined level of stride width magnitude.

14. The walking posture determination apparatus according to claim 13, wherein
the storage device stores associations between walking posture levels and index values of a plurality of indices representing walking posture, and stores associations between types of walking postures and combinations of walking posture levels or index values of the plurality of indices representing walking posture, and
the processor is programmed to:
determine a type of walking posture in accordance with the calculated index value, and
display the type of walking posture determined as the walking posture determination result.

15. The walking posture determination apparatus according to claim 13, wherein the processor is programmed to:
determine the walking posture level for each of a plurality of indices representing walking posture, and
display, on a screen, the determined walking posture levels using a single graph whose axes respectively indicate the indices.

16. The walking posture determination apparatus according to claim 13, wherein the processor is programmed to display the walking posture level on a screen, as the walking posture determination result, using a bubble chart in which a position or a size of a displayed graphic are selected based on the determined walking posture level.

17. The walking posture determination apparatus according to claim 13, wherein the processor is programmed to:
accept input of a walking posture level as a target level,
calculate a difference between the determined walking posture level and the input walking posture level, and
output the calculated difference.

18. The walking posture determination apparatus according to claim 13, wherein the processor is programmed to perform at least one of output using a display screen, output using a vibrating apparatus, output using light, and output using audio.

* * * * *